(12) United States Patent
Schuehrer

(10) Patent No.: US 7,552,823 B2
(45) Date of Patent: Jun. 30, 2009

(54) PACKAGING WITH APPLICATOR

(75) Inventor: Herbert Schuehrer, Bruchsal (DE)

(73) Assignee: Klocke Verpackungs-Service GmbH, Weingarten (DE)

(*) Notice: Subject to any disclaimer, the term of this patent is extended or adjusted under 35 U.S.C. 154(b) by 210 days.

(21) Appl. No.: 11/528,593

(22) Filed: Sep. 28, 2006

(65) Prior Publication Data

US 2007/0068845 A1  Mar. 29, 2007

(30) Foreign Application Priority Data

Sep. 28, 2005 (DE) .................. 20 2005 015 085 U

(51) Int. Cl.
B65D 75/36 (2006.01)
(52) U.S. Cl. .................. 206/484; 206/469; 206/581
(58) Field of Classification Search ............ 206/581, 206/484, 274, 484.1, 207, 209, 229, 230, 206/469, 219, 220, 261, 568; 222/187, 215, 222/106, 107, 92, 541.4, 541.6; 229/56, 229/120, 922; 383/207, 208; 239/34, 57, 239/36, 60; 401/132, 133; 604/3
See application file for complete search history.

(56) References Cited

U.S. PATENT DOCUMENTS

| | | | | |
|---|---|---|---|---|
| 3,035,300 A | * | 5/1962 | Wattles | 401/198 |
| 3,053,385 A | * | 9/1962 | Spees | 206/361 |
| 3,315,801 A | * | 4/1967 | Lowry | 206/469 |
| 3,369,267 A | * | 2/1968 | Friedland et al. | 15/104.94 |
| 3,635,376 A | * | 1/1972 | Hellstrom | 222/107 |
| 4,140,409 A | * | 2/1979 | DeVries | 401/132 |
| 4,236,652 A | * | 12/1980 | Beguhn | 222/92 |
| 4,430,013 A | * | 2/1984 | Kaufman | 401/132 |
| 4,493,574 A | * | 1/1985 | Redmond et al. | 401/132 |
| 4,611,715 A | * | 9/1986 | Redmond | 206/484 |
| 4,871,091 A | * | 10/1989 | Preziosi | 222/92 |
| 5,316,400 A | * | 5/1994 | Hoyt et al. | 401/132 |
| 5,395,031 A | * | 3/1995 | Redmond | 222/541.6 |
| 5,562,642 A | * | 10/1996 | Smith et al. | 604/289 |
| 6,007,264 A | * | 12/1999 | Koptis | 401/132 |
| 6,041,930 A | * | 3/2000 | Cockburn | 206/484 |
| 6,405,868 B1 | * | 6/2002 | Bougamont et al. | 206/484 |
| 6,705,541 B2 | * | 3/2004 | Schuehrer et al. | 239/34 |
| 7,121,409 B1 | * | 10/2006 | Hamilton et al. | 206/484.2 |

(Continued)

FOREIGN PATENT DOCUMENTS

WO  0009414 A1  2/2000

*Primary Examiner*—J. Gregory Pickett
*Assistant Examiner*—Andrew Perreault
(74) *Attorney, Agent, or Firm*—Browdy and Neimark, P.L.L.C.

(57) ABSTRACT

A packaging is composed of two foils joined along their edges that enclose at least one chamber containing a carrier provided, or to be provided, with a medium. A first foil has extending in it a predetermined break line for exposing the carrier, over which the carrier extends. Disposed between the second foil and the carrier is a largely rigid insert that extends beyond the predetermined break line situated opposite from it, at least far enough so that when the packaging is broken open, the carrier is pulled out of the chamber by a corresponding distance for removal or application of the medium. The insert acts as an "expelling sheet" between the carrier and covering foil and is dimensioned to either extend in its end contour beyond the predetermined break line or, upon bending at a weakening, portions of the insert extend beyond the predetermined break line.

9 Claims, 3 Drawing Sheets

U.S. PATENT DOCUMENTS 7,240,797 B1 * 7/2007 Grossman .................. 206/551
2006/0283727 A1 * 12/2006 Nelson et al. ............... 206/219
2007/0138204 A1 * 6/2007 Chen et al. ............... 222/145.1

* cited by examiner

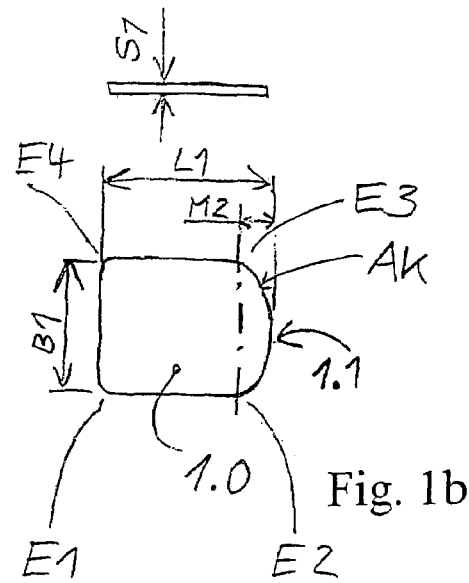
Fig. 1a
Fig. 1b
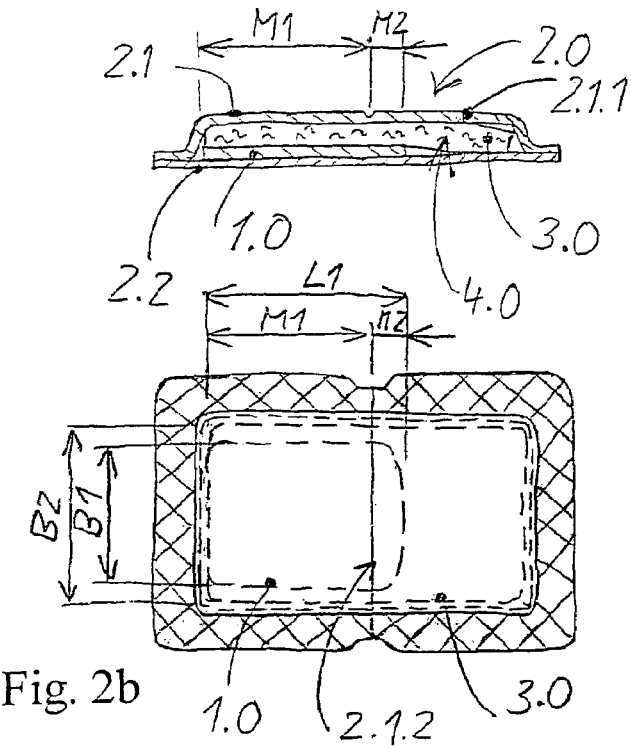
Fig. 2a
Fig. 2b
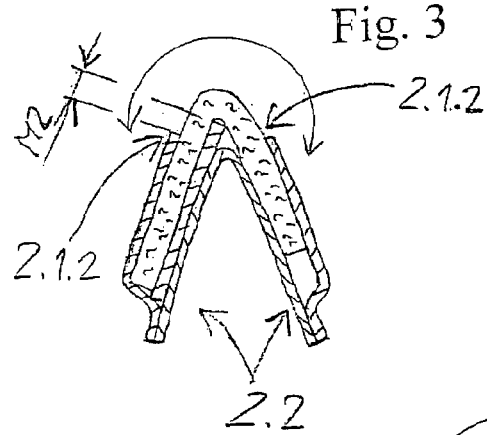
Fig. 3
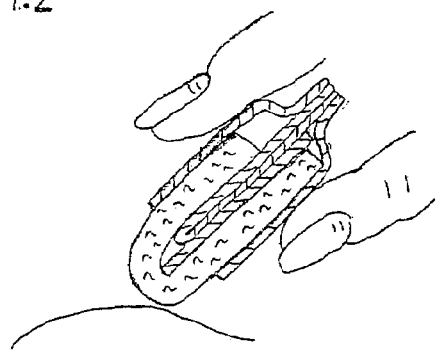
Fig. 4

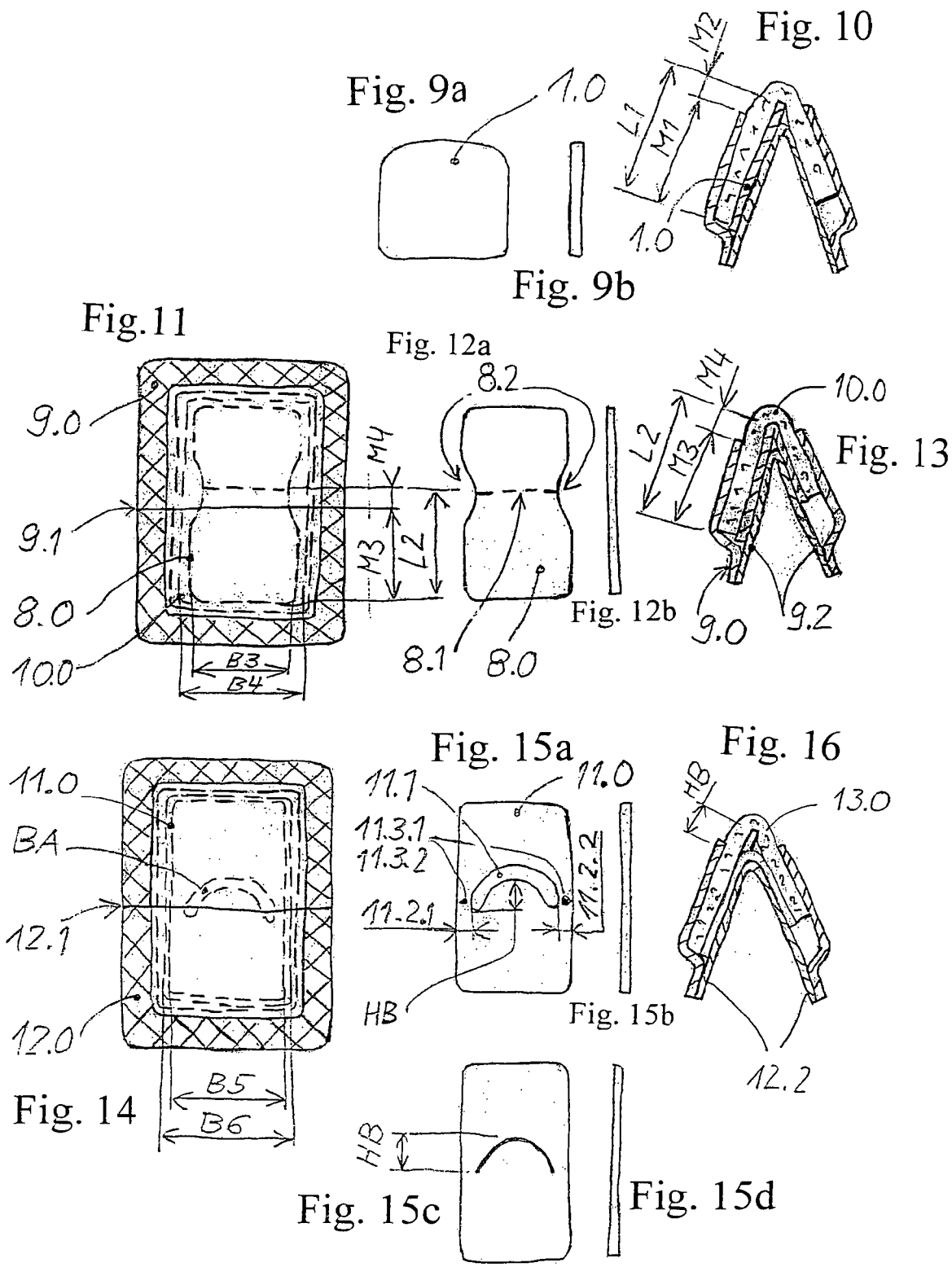

PACKAGING WITH APPLICATOR

BACKGROUND OF THE INVENTION

The present invention relates to a packaging composed of two foils joined along their edges and enclosing at least one chamber containing a carrier provided, or to be provided, with a medium, wherein a first foil has extending in it a line-shaped predetermined break point for exposing the carrier, over which the carrier extends.

In medicine, cosmetics, or chemical applications, absorbent carriers, e.g., in the form of sponges or felts, are used for storing or for applying liquid and pasty media, or for presenting fragrance samples. Also in use are flexible carriers composed of absorptive material, such as synthetic material, paper, or cardboard. These absorbent carriers are customarily saturated with the medium to be used. The saturated absorbent carrier, depending on the application, may also be used as an applicator to wet the areas that are to be supplied with the medium.

If the medium to be applied is taken from larger packaging containers, there is a risk of unintentional contact with the medium or also of contaminating it. In an effort to find a remedy, packaging units for one-time use have been developed that permit a largely hygienic operation for the layperson as well.

One example for applications of this type are packaging units incorporating a predetermined break point, which may contain both the medium to be applied, a well as an applicator.

In order to optimally protect the product, the user, and areas to be wetted, the applicator is inserted into the depression of a preferably thermoformed plastic foil in such a way that the applicator may be wetted with the medium to be applied. In other packaging variations, the medium to be applied is located in a separate depression. The depressions are preferably covered by a covering foil, which is applied preferably by sealing, and they are thus protected against external influences.

Extending in the region of the depression of the packaging for the applicator is a predetermined break point. If the medium to be applied is stored in a separate depression, it is combined with the applicator immediately prior to the application process. In order to make use of the applicator, the packaging is opened by bending and cracking it at the predetermined break point. The two ends of the packaging are subsequently doubled back toward the covering foil, so that the applicator is exposed in the region of the predetermined break point. The medium to be applied is now ready to be used.

It is a shortcoming of packaging of this type that the applicator projects beyond the broken open region of the packaging only to a small degree, so that there is a risk that the outer portion of the packaging or the break point area can come into contact with the part to be wetted. Especially in the medical field, where packaging of this type is used, for example, for wound care, germs may be transferred here from contaminated outer surface of packaging of this type to the area to be treated, or the area to be treated may be affected by the edge of the break point of the packaging.

BRIEF SUMMARY OF THE INVENTION

It is an aim of the invention to force the respective carrier or applicator further out from the packaging without the aid of external means, to be precise.

This is achieved by a packaging according to the invention composed of: first and second foils joined along their edges that enclose at least one chamber containing a carrier provided or to be provided with a medium, wherein the first foil is formed to have a line-shaped first predetermined break line for exposing the carrier, the break line extending over the carrier; a largely rigid insert disposed between the second foil and the carrier, the insert extending beyond the first predetermined break line at least far enough so that when the packaging is broken open, the carrier is pulled out of the chamber by a corresponding distance for removal or application of the medium.

The inventive insert acts as an "expelling sheet" between the carrier and the covering foil, which is selected with respect to its dimension such that it either extends in its end contour beyond the predetermined break point, or that, upon bending at a weakening, portions of the insert extend beyond the predetermined break point. The carrier or applicator is forced to wrap itself over the region of the insert that extends beyond the predetermined break point. As a result, the carrier is pulled further out from the packaging.

Use of the packaging is thereby made safer, the risk of contamination caused by the outer skin, or surface, of the packaging, and also the possibility of injury caused by the edge of the break point, are thereby minimized.

Additional embodiments will become apparent from the following description.

BRIEF DESCRIPTION OF THE DRAWINGS

FIGS. 1a and 1b are front and top views, respectively, of a first embodiment of the invention.

FIGS. 2a and 2b are cross-sectional front and top views, respectively, of packaging according to the invention with an insert.

FIG. 3 is a cross-sectional front view of an opened packaging with an insert.

FIG. 4 is a view similar to FIG. 3 showing an application performed with the packaging of FIG. 3.

FIGS. 9a and 9b are views similar to those of FIGS. 1a and 1b, respectively, showing a first embodiment of the insert.

FIG. 10 is a view similar to FIG. 3 showing the insert in an activated packaging, in connection with the first exemplary embodiment.

FIG. 11 is a view similar to FIG. 2b relating to a second embodiment of the insert.

FIGS. 12a and 12b are views similar to those of FIGS. 9a and 9b of the second embodiment of the insert.

FIG. 13 is a view similar to FIG. 3 showing the insert in an activated packaging, in connection with the second embodiment.

FIG. 14 is a view similar to FIG. 2b relating to a third embodiment of the insert.

FIGS. 15a and 15b are views similar to those of FIGS. 9a and 9b of the third embodiment of the insert.

FIGS. 15c and 15d are views similar to those of FIGS. 9a and 9b of a variation of the third embodiment of the insert.

FIG. 16 is a view similar to FIG. 3 showing the insert in an activated packaging, in connection with the third embodiment.

DETAILED DESCRIPTION OF THE INVENTION

Figure 5:
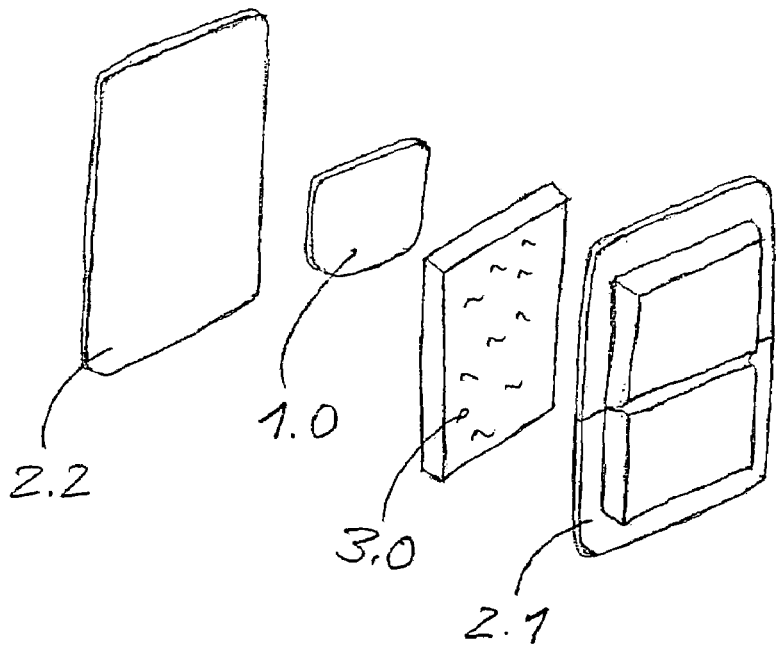
FIG. 5 is an exploded perspective view of the packaging with an insert.

FIGS. 1 through 5 show a first exemplary embodiment of a cupped packaging with a predetermined break line 2.1.2 in a bottom foil 2.1 and an insert 1.0. FIGS. 1a and 1b show the insert 1.0 in a front view and in a top view, respectively. FIGS. 2a and 2b show a cross section through a packaging with an insert 1.0 and a top view, respectively. FIGS. 3 and 4 show an opened packaging with insert and application of a medium with the insert, respectively. FIG. 5 shows an exploded view of the packaging with insert 1.0.

Insert 1.0 is preferably composed of plastic and it is placed in a cupped packaging 2.0 consisting of the preferably thermoformed bottom foil 2.1 incorporating a depression 2.1.1 constituting a receptacle for an applicator 3.0, insert 1.0 being positioned between applicator 3.0 and covering foil 2.2, which is preferably attached to foil 2.2 by sealing foil 2.2 to the circumferential parts of foil 2.1. Applicator 3.0 in this embodiment is already wetted with a medium 4.0 to be applied. Receptacle depression 2.1.1 is provided with a line-shaped weakening of the material as the predetermined break line 2.1.2.

Insert 1.0 is designed in its dimension L1 in such a way that it exceeds by the dimension M2, the dimension M1, which approximately represents the distance between one end of receptacle indention 2.1.1 for applicator 3.0 and the predetermined break line 2.1.2. The width B1 of insert 1.0 is preferably kept slightly smaller than the width B2 of applicator 3.0. Insert 1.0 may be rounded at its corners E1, E2, E3, E4, in order to reduce the risk of injury. An outward curvature 1.1 of the outer contour AK of insert 1.0 in the region that will later be the pulled section, i.e., the section that projects out of the opened package, allows applicator 3.0 to slide at least partially out of packaging 2.0 more easily. Upon activation of packaging 2.0 by breaking it open along the predetermined break line 2.1.2 and subsequently bringing the packaging ends together so that the two parts of covering foil 2.2 face, and approach, one another (FIG. 3), a projecting length M2 of insert 1.0 emerges from packaging 2.0 at the predetermined break line 2.1.2. Applicator 3.0 that is situated above insert 1.0 is forced to wrap itself over edge AK associated with projecting length M2, causing applicator 3.0 to be pulled further out from the insert-free portion of the packaging. The thickness S1 of insert 1.0 may be selected in dependence upon the material and manufacturing process and, depending on the stiffness of the material, is preferably in a range between 0.3 and 3 mm.

Figure 6A:
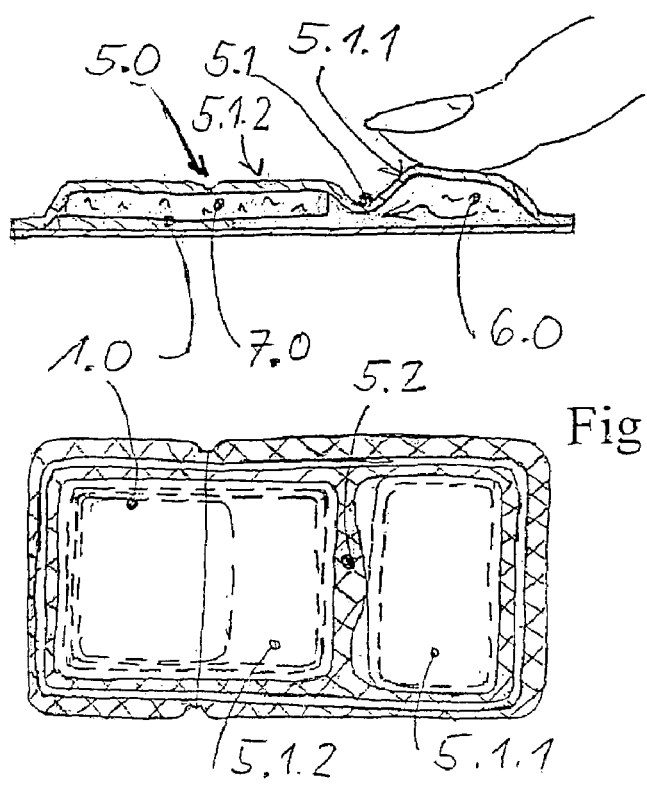
FIGS. 6a, 6b, 7 and 8 are views similar to FIGS. 2a, 2b, 3 and 4, respectively, showing a second exemplary embodiment, which is a dual-chamber packaging with an insert and a predetermined break point.
Figure 7:
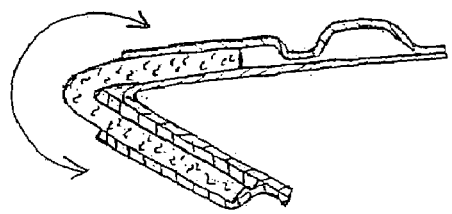
Figure 6B:
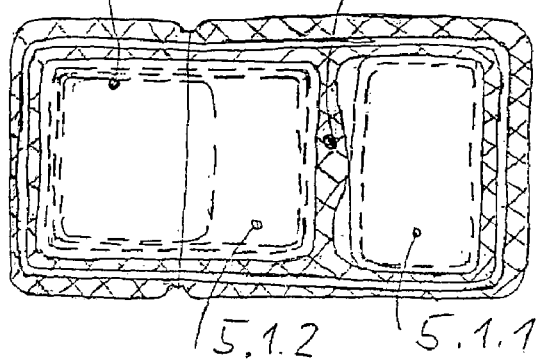
Figure 8:
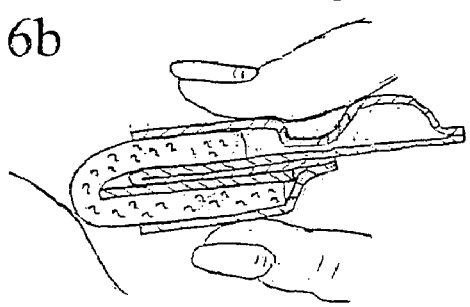

FIGS. 6 through 8 show an additional exemplary embodiment constituted by a cupped packaging 5.0 with predetermined break line 5.1.3 in a bottom foil 5.1 that is sealed around its circumference to a cover foil. This embodiment is in the form of a 2-component packaging provided with an insert 1.0. The function of this embodiment corresponds to that described above with respect to the first embodiment. A medium 6.0 to be applied is stored here in a separate depression 5.1.1 of bottom foil 5.1. In a region 5.2 located between depression 5.1.1 for medium 6.0 and a depression 5.1.2 for the applicator 7.0, the bottom foil and cover foil are joined together by a week seal. By applying pressure to bottom foil 5.1 in the region of depression 5.1.1, the seal will be broken, allowing medium 6.0 to flow into depression 5.1.2 so that applicator 7.0 is wetted with the medium to be applied shortly prior to the application process, without the contents of the packaging coming into contact with exterior surfaces.

FIGS. 9 through 15 show several basic embodiments of the insert.

FIGS. 9a and 9b show an insert 1.0 as described in the first example embodiment. FIG. 10 shows the insert 1.0 in an activated packaging, as described in connection with the first exemplary embodiment.

FIGS. 11 through 13 show, according to a second embodiment of the insert, an insert 8.0. FIG. 11 shows a packaging with insert 8.0 in a top view, FIGS. 12a and 12b show insert 8.0 in a top and side view, respectively. FIG. 13 shows insert 8.0 when the packaging has been opened.

Insert 8.0 is intended for a packaging 9.0 with a predetermined break line 9.1 corresponding to the embodiments previously described. However, insert 8.0 extends in its longitudinal dimension over a significant portion of applicator 10.0.

Insert 8.0 is provided with a weakening line 8.1, e.g., in the form of a perforation or scoring. Weakening line 8.1 is arranged on insert 8.0 in such a way that it extends inside packaging 9.0 parallel to the predetermined break line 9.1 of packaging 9.0. The dimension L2, which determines the position of weakening line 8.1, is dimensioned such that, when placing insert 8.0 into packaging 9.0, dimension L2 exceeds by the dimension M4, the dimension M3, which represents approximately the distance between one end of the receptacle bowl for applicator 10.0 and the predetermined break line 9.1. The width B3 of insert 8.0 is preferably slightly smaller than the width B4 of applicator 10.0. A narrowing 8.2 in the region of the weakening line 8.1 reduces a risk of injury from insert 8.0 in this area.

Upon activation of packaging 9.0 by breaking it open along the predetermined break line 9.1 and subsequently bringing together the packaging ends toward the parts of covering foil 9.2, insert 8.0 is folded and cracked at its weakening line 8.1, with the projecting length M4 of insert 8.0 extending from packaging 9.0 beyond the predetermined break line 9.1. Applicator 10.0 that is situated above insert 8.0 is forced to wrap itself over this projecting length M4, during which process it is pushed out of the packaging by a distance defined by the projecting length M4.

FIGS. 14 through 16 show an additional exemplary embodiment of the packaging with an insert 11.0. Insert 11.0 is intended for a packaging 12.0 having a predetermined break line 12.1 corresponding to the previous embodiments. Insert 11.0 extends, like in the second embodiment, over a significant portion of applicator 13.0.

Insert 11.0 is provided with a weakening area 11.1, e.g., in the form of a punched out portion (FIG. 15a) or in the form of a cut (FIG. 15c). The weakening area 11.1 is preferably formed to have an arc shape, although other shapes are possible, in insert 11.0 in such a way that the ends of the arc BA, upon insertion into packaging 12.0 comes to rest approximately at the position of the predetermined break line 12.1 of packaging 12.0. The width of the punched out area or cut 11.1 is designed such that insert 11.0 experiences its greatest weakening at the webs 11.2.1 and 11.2.2 remaining at the ends of the punched out area. Embossing or perforations 11.3.1 and 11.3.2 in this region can increase the weakening even further. The height HB of the inside curve of the punched out portion or cut 11.1 determines the degree by which applicator 13.0 is forced out of packaging 12.0 in the region of the predetermined break line 12.1. The width B5 of insert 11.0 is preferably slightly smaller than the width B6 of applicator 13.0.

Upon activation of packaging 12.0 by breaking it open along the predetermined break line 12.1 and subsequently bringing together the packaging ends toward the parts of covering foil 12.2, insert 11.0 is folded and cracked at its weakening 11.2.1, and 11.2.2 with the arc-shaped region having height HB of insert 11.0 extending from packaging 12.0 beyond the predetermined break line 12.1 of package 12.0. Applicator 10.0 that is situated above insert 11.0 is forced to wrap itself over the arc-shaped region and is consequently pulled further out from packaging 12.0.

The examples listed so far only serve to illustrate the function of the insert. An insert of this type may be used in any packaging in which partial areas of an applicator are to be forced out, and which have a similar opening mechanism.

This application relates to subject matter disclosed in German Application Number 20 2005 015 085.1, filed on Sep. 28, 2005, the disclosure of which is incorporated herein by reference.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A packaging comprising: first and second foils joined along their edges that enclose at least one chamber and a carrier of absorptive material contained in said chamber and provided or to be provided with a medium, wherein said first foil is formed to have a line-shaped first predetermined break line, which extends over the carrier, for exposing the carrier; a largely rigid insert disposed between said second foil and said carrier, said insert extending beyond the first predetermined break line at least far enough so that when the packaging is broken open, said carrier is pulled out of the chamber by a corresponding distance for removal or application of the medium, and further wherein said insert forms an expelling sheet dimensioned and operative to move said carrier out of said packaging when said packaging is broken open.

2. The packaging according to claim 1, wherein said packaging is a cupped packaging, and said first foil incorporating the predetermined break line is a cupped bottom foil of said packaging.

3. The packaging according to claim 1, wherein said insert has a first width and said carrier has a second width parallel to said break line that is slightly larger than said first width.

4. The packaging according to claim 1, wherein said first break line is located substantially midway between opposed ends of said packaging.

5. The packaging according to claim 1, wherein said insert has a second predetermined break line extending parallel to, and at a distance from, said first predetermined break line.

6. The packaging according to claim 5, wherein said insert has lateral narrowings in line with said second predetermined break line.

7. The packaging according to claim 1, wherein said insert has a weakening in the form of a punched out area or cut extending in an arc shape from two lateral bending points that are in line with said first predetermined break line so that a loop is formed, which upon breaking said packaging open along said first predetermined break line, pulls said carrier partly out of said at least one chamber.

8. The packaging according to claim 1, constituted by a dual-chamber packaging, wherein said at least one chamber comprises separate first and second chambers, said first chamber being provided with said first predetermined break line, said carrier being accommodated in said first chamber, and the medium being accommodated in said second chamber and being transferable to said first chamber by exertion of pressure said the second chamber.

9. The packaging according to claim 1, wherein said carrier is an applicator for applying the medium.

* * * * *